United States Patent [19]
Edwards

[11] 3,998,961
[45] * Dec. 21, 1976

[54] FUNGICIDAL SULFONAMIDOTHIOPHENES

[75] Inventor: Laroy H. Edwards, Napa, Calif.

[73] Assignee: Chevron Research Company, San Francisco, Calif.

[ * ] Notice: The portion of the term of this patent subsequent to June 10, 1992, has been disclaimed.

[22] Filed: May 19, 1975

[21] Appl. No.: 578,559

Related U.S. Application Data

[63] Continuation-in-part of Ser. No. 489,310, June 29, 1974, Pat. No. 3,888,879.

[52] U.S. Cl. ............................ 424/275; 260/329 S
[51] Int. Cl.$^2$ ...................................... A01N 9/16
[58] Field of Search ................ 424/275; 260/329 S

[56] References Cited
UNITED STATES PATENTS 3,888,879    6/1975    Edwards ...................... 260/329 S

OTHER PUBLICATIONS

Chemical Abstracts 72:111289g (1970).

Chemical Abstracts 65:12157e (1966).

Primary Examiner—Leonard Schenkman
Attorney, Agent, or Firm—G. F. Magdeburger; Dix A. Newell; Raymond Owyang

[57] ABSTRACT

Novel thiophenes of the formula

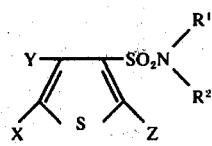

wherein X and Z individually are nitro, fluoro, chloro or bromo, Y is hydrogen, nitro, fluoro, chloro or bromo, $R^1$ is alkyl or aryl and $R^2$ is hydrogen or haloalkylthio, are useful for the prevention or cure of fungal infections.

15 Claims, No Drawings

FUNGICIDAL SULFONAMIDOTHIOPHENES

CROSS-REFERENCE TO RELATED APPLICATION

This application is a continuation-in-part of application Ser. No. 489,310, filed June 29, 1974, now U.S. Pat. No. 3,888,879, the disclosure of which is incorporated herein by reference.

DESCRIPTION OF THE PRIOR ART

French Pat. No. 1,563,736, issued Apr. 18, 1969, to Pillon et al, discloses pesticidal 2-sulfonamido-3,4,5-trichlorothiophenes. A. Buzas et al, "Ann. Pharm. France" 19, 449 (1961) [C.A. 56, 6603c (1962)] discloses diuretic 2-sulfonamidothiophenes.

DESCRIPTION OF THE INVENTION

The thiophenes of the invention are represented by the formula

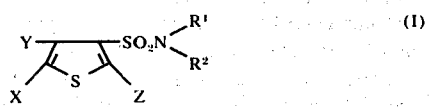

wherein X is nitro, fluoro, chloro or bromo; Y is hydrogen, nitro, fluoro, chloro or bromo; $R^1$ is alkyl of 1 to 6 carbon atoms, phenyl substituted with up to 2 (0 to 2) of the same or different substituents selected from trifluoromethyl, trichloromethyl, fluoro, chloro, bromo, iodo, nitro or alkyl of 1 to 3 carbon atoms; and $R^2$ is hydrogen or haloalkylthio of 1 to 3 carbon atoms and 1 to 7 of the same or different halogens of atomic number 9 to 35 fluoro, chloro or bromo).

Representative alkyl $R^1$ groups are methyl, ethyl, propyl, isopropyl, butyl and hexyl. Representative substituted phenyl $R^1$ groups are o-trifluoromethylphenyl, m-trifluoromethylphenyl, p-trichloromethylphenyl, o-fluorophenyl, m-chlorophenyl, p-bromophenyl, 2,4-dichlorophenyl, 3,5-dibromophenyl, 3-bromo-4-chlorophenyl, o-tolyl, 2,4-dimethylphenyl, p-nitrophenyl and 2-chloro-4-methylphenyl. Representative haloalkylthio $R^2$ groups are chloromethylthio, trifluoromethylthio, dichloromethylthio, trichloromethylthio, fluorodichloromethylthio, tribromoethylthio, 2,2,2-trichloroethylthio, 1,2,2,2-tetrachloroethylthio, 1,1,2,2-tetrabromoethylthio, pentachloroethylthio, 2,2,3,3,3-pentabromopropylthio and 3,3,3-trichloropropylthio.

The preferred Y group is hydrogen, nitro, chloro or bromo. The preferred X and Z groups are chloro or bromo. The preferred $R^1$ group is lower alkyl of 1 to 3 carbon atoms or phenyl substituted with 1 to 2 trifluoromethyl or trichloromethyl. The preferred $R^2$ group is hydrogen or haloalkylthio of 1 to 2 carbon atoms and 2 to 5 of the same or different halogens selected from chloro or bromo.

A preferred class of thiophenes of formula (I) is that wherein X is chloro or bromo, Y is hydrogen, nitro, chloro or bromo, Z is chloro or bromo, $R^1$ is phenyl substituted with 1 to 2 trifluoromethyl or trichloromethyl, and $R^2$ is hydrogen.

Another preferred class of thiophenes of formula (I) is that wherein X is chloro or bromo, Y is hydrogen, nitro, chloro or bromo, Z is chloro or bromo, $R^1$ is alkyl of 1 to 3 carbon atoms or phenyl substituted with up to 2 of the same or different substituents selected from trifluoromethyl, trichloromethyl, chloro or alkyl of 1 to 3 carbon atoms, and $R^2$ is haloalkylthio of 1 to 2 carbon atoms and 2 to 5 of the same or different halogens selected from chloro or bromo.

The thiophenes of the invention wherein $R^2$ is hydrogen are prepared by reacting a thienylsulfonyl chloride (II) with an amine or aniline compound (III). The thiophenes of the invention wherein $R^2$ is haloalkylthio are prepared by sulfenylating the resulting sulfonamidothiophene (IV) with a haloalkylsulfenyl halide (V) in the presence of an acid acceptor. These reactions are depicted in reactions (1) and (2):

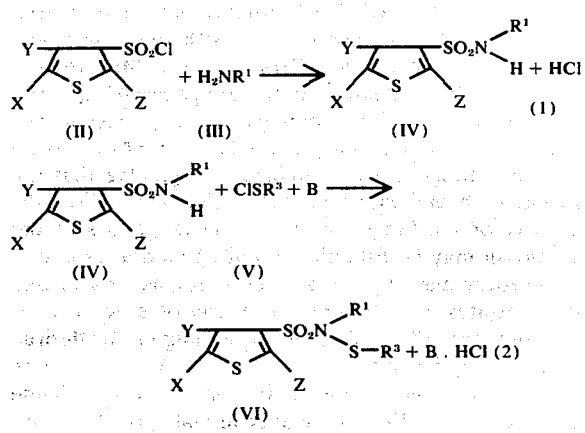

wherein X, Y, Z and $R^1$ have the same significance as previously defined, $SR^3$ is a haloalkylthio $R^2$ group as previously defined, and B is an acid acceptor.

Reaction (1) is conducted by reacting substantially equimolar quantities of the thienylsulfonyl chloride (II) and the amine or aniline (III) in an inert diluent at a temperature of 0° to 100° C. If desired, a molar excess of the amine or aniline (III), or an acid acceptor as defined below, can be used as an acid acceptor for the hydrogen chloride produced in the reaction. Reaction (2) is conducted by reacting substantially equimolar quantities of the sulfonamidothiophene (IV) and the sulfenyl halide (V) in the presence of an acid acceptor. Suitable acid acceptors are organic amines such as pyridine compounds, e.g., pyridine or alpha-picoline, and lower trialkylamines, e.g., triethylamine or tripropylamine. Generally, at least one mol of acid acceptor is employed for each mol of sulfenyl halide. The reaction is normally conducted in an inert liquid diluent, e.g., organic solvents such as chlorinated hydrocarbons. The product (I) is isolated and purified by conventional procedures such as extraction, filtration, crystallization and chromatography.

The 2,5-dihalothienylsulfonyl chlorides of formula (II) are suitably prepared by sulfonating a 2,5-dihalothiophene with chlorosulfonic acid. The 2,4,5-trihalothienylsulfonyl chlorides of formula (II) are suitably prepared by halogenating the 2,5-dihalothienylsulfonyl chloride. The nitrohalothienylsulfonyl chlorides of formula II are suitably prepared by nitrating a halothienylsulfonyl chloride with nitric acid in a suitable solvent such as concentrated sulfuric acid or acetic anhydride.

The compounds of the invention are useful for controlling fungi, particularly plant fungal infections caused by *Botrytis cinerea*, leaf blights caused by organisms such as *Septoria apii*, *Alternaria solani conidia* and *Phytophthora infestans conidia*, powdery mildew caused by organisms such as *Erysiphe polygoni* and *E. chicoraciarum*, and other fungal infections caused by organisms such as *Pythrium ultimum*, *Helminthosporum sativum*, *Fusarium moniliforme*, *Rhizoctonia solani*, *Monolinia frucicola* and *Uromyces phaseoli typica*. However, some fungicidal compounds of the invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divide particles which disperse readily in water or other dispersant. These compositions normally contain from about 5–80% fungicide, and the rest inert material, which includes dispersing agents, emulsifying agents, and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier, such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of these these techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLE 1

Preparation of 2,5-dichloro-3-(N-methylsulfonamido) thiophene and 2,5-dichloro-3-(N-methyl-N-1,1,2,2-tetrachloroethylthiosulfonamido) thiophene A 96.8-g (0.632 mol) sample of 2,5-dichlorothiophene was added dropwise to a cooled (dry ice/acetone bath, about −10° to −15° C) and stirred solution of 163 g (1.39 mol) of chlorosulfonic acid. After the addition was completed, the reaction mixture was stirred at 50° C for 2 hours, cooled, and then poured into 200 g of ice. The aqueous reaction mixture was extracted with methylene chloride. The methylene chloride extract was washed with saturated aqueous sodium bicarbonate solution, washed with water, dried over magnesium sulfate, and evaporated to give 87 g of 2,5-dichloro-3-thienylsulfonyl chloride.

A 10.5-g (0.34 mol) sample of methylamine in about 15 ml water was added dropwise to 43 g of the 2,5-dichloro-3-thienylsulfonyl chloride prepared above. After the addition was completed, the reaction mixture was heated at 50° C for 2 hours. The reaction mixture was then cooled, diluted with methylene chloride, washed with water, dried over magnesium sulfate and evaporated to give 41.6 g of 2,5-dichloro-3-(N-methylsulfonamido)thiophene.

A 12.7-g (0.05 mol) sample of 1,1,2,2-tetrachloroethylsulfenyl chloride was added slowly to a cooled (−10° C) solution of 12.5 g (0.05 mol) 2,5-dichloro-3-(N-methylsulfonamido)thiophene in 200 ml methylene chloride. To the resulting solution was then added dropwise 5.6 g (0.055 mol) triethylamine at −5° to 0° C. The reaction mixture was stirred at about 25° C for 2½ hours, washed with water, dried over magnesium sulfate and evaporated to give the product as a oil which crystallized from hexane as a white solid, m.p. 85°–86° C.

EXAMPLE 2

Preparation of 2,5-dichloro-3-(N-methylsulfonamido)thiophene and 2,5-dichloro-3-N-methyl-N-trichloromethylthiosulfonamido)thiophene A 5.6-g (0.055 mol) sample of triethylamine was added dropwise to a solution of 12.5 g (0.05 mol) 2,5-dichloro-3-(N-methylsulfonamido)thiophene and 9.3 g (0.05 mol) trichloromethylsulfenyl chloride at −5° to 0° C. The reaction mixture was then stirred at about 25° C for 2½ hours, washed with water, dried over magnesium sulfate and evaporated to give the product as an oil which crystallized as a white solid, m.p. 89°–91° C, when slurried with hexane.

EXAMPLE 3

Preparation of 2,4,5-trichloro-3-(N-p-tolylsulfonamido)thiophene and 2,4,5-trichloro-3-(N-p-tolyl-N-trichloromethylthiosulfonamido)thiophene A mixture of 63 g (0.25 mol) 2,5-dichlorothien-3-ylsulfonyl chloride, 0.5 g sulfur monochloride and 25 g sulfuryl chloride was heated under reflux. To the refluxing reaction was then added dropwise 0.5 g aluminum trichloride in 25 g sulfuryl chloride. The reaction mixture was then heated under reflux for 3 hours, cooled diluted with 400 ml cold water and cooled, with methylene chloride. The methylene chloride extracts were washed with water, saturated aqueous sodium bicarbonate, dried over magnesium sulfate and stripped to give 62 g of 2,4,5-trichlorothien-3-ylsulfonyl chloride, which crystallized from hexane as a solid, m.p. 55° C.

A solution of 21.4 g (0.2 mol) p-toluidine in methylene chloride was added dropwise to a solution of 28.6 g (0.2 mol) 2,4,5-trichlorothien-3-ylsulfonyl chloride in methylene chloride (200 ml total) at about −60° C. The reaction mixture was allowed to warm to about 25° C with stirring and then stirred at 25° C for 1 hour. The reaction was filtered and the filtrate was washed with water, dried over magnesium sulfate and evaporated to give 30 g of 2,4,5-trichloro-3-N-p-tolylsulfonamido)-thiophene, m.p. 124°–125° C.

A 30-g (0.03 mol) sample of triethylamine was added dropwise to a solution of 80 g (0.022 mol) 2,4,5-trichloro-3-(N-p-tolylsulfonylamido)thiophene and 4.2 g (0.022 mol) trichloromethylsulfenyl chloride in 150 ml methylene chloride at −10° C. The reaction mixture was allowed to warm to about 25° C and then stirred at about 25° C for 1 hour. The reaction mixture was washed with water, dried over magnesium sulfate and stripped to give the 2,4,5-trichloro-3-(N-p-tolyl-N-trichloromethylthiosulfonamido)thiophene product, as an oil which crystallized from ether-hexane as a white solid, m.p. 111°–112° C.

EXAMPLE 4

Preparation of 2,5-dichloro-4-nitro-3-(N-p-trifluoromethylphenylsulfonamido)thiophene A 55.8-g (0.22 mol) sample of 2,5-dichloro-3-thienylsulfonyl chloride was added in small portions to a stirred solution of 150 ml concentrated nitric acid and 150 ml concentrated sulfuric acid. After the addition was completed, the reaction mixture was stirred at about 25° C overnight. The reaction mixture was then diluted with ice water and filtered to give the crude 2,5-dichloro-4-nitro-3-thienylsulfonyl chloride product. The product was washed with water and dried. Recrystallization from methylene chloride gave the product as a brown solid, m.p. 89°–91° C.

A 9.2-g (0.031 mol) sample of 2,5-dichloro-4-nitro-3-thienylsulfonyl chloride was added in small portions to a solution of 10 g (0.062 mol) p-trifluoromethylaniline in 150 ml methylene chloride. The reaction mixture was allowed to stir overnight at about 25° C. A 3.5-g (0.035 mol) sample of triethylamine was then added and the resulting reaction mixture stirred overnight at about 25° C. The reaction mixture was then washed with water, dried over magnesium sulfate and stripped to give the 2,5-dichloro-4-nitro-3-(N-p-trifluoromethylphenylsulfonamido)thiophene product as a yellow solid, m.p. 160°–163° C.

EXAMPLE 5

Preparation of 2,5-dichloro-3-(N-p-trifluoromethylphenylsulfonamido)thiophene

A solution of 39 g (0.155 mol) of 2,5-dichloro-3-thienylsulfonyl chloride in methylene chloride was added dropwise over 90 minutes to a cooled solution (−60° C) of 50 g (0.31 mol) p-trifluoromethylaniline. The reaction mixture was then allowed to warm to about 25° C and stirred overnight.

The reaction mixture was then filtered, washed with water and evaporated to give a solid. The solid was crystallized from hexane to give the 2,5-dichloro-3-(N-p-trifluoromethylphenylsulfonamido)thiophene product, as a yellow solid, m.p. 102°–103° C.

Other compounds of the invention were prepared by the procedures of Examples 1–5. These compounds and the compounds of Examples 1–5 are tabulated in Table I.

EXAMPLE 6

*Botrytis cinerea* control

Representative compounds of the invention were tested for *Botrytis cinerea* control using detached, well-developed primary leaves of a 4–6 week old horsebean plant. The leaves were dipped into a 40–ppm solution of the test compound in acetone and water containing a small amount of a nonionic emulsifier, then taken out and placed in a petri plate lined with two pieces of filter paper. The leaves were allowed to dry while the filter paper was kept moist by adding water as required. The treated leaves were then inoculated with the spores of *Botrytis cinerea* fungus grown on potato dextrose agar plates. The plates were covered after inoculation and kept at 23.5° C. The filter-paper linings of the plates were kept saturated with water throughout the test. The rate of disease incidence was determined in 3 to 5 days, when the disease symptoms were fully evident on non-treated check leaves. The percentage disease control provided by the test compound was calculated as the percentage disease reduction based on the non-treated check leaves. The test compounds and the results are tabulated in Table II. For comparison, 2,5-dichloro-3-(N-methylsulfonamido)thiophene and 5-chloro-2-(N-methyl-N-trichloromethylthiosulfonamido)thiophene were also tested.

EXAMPLE 7

Tomato Late Blight

Representative compounds of the invention were tested for the control of the Tomato Late Blight organism *Phytophthora infestans conidia*. Five- to six-week-old tomato (variety Bonny Best) seedlings were used. The tomato plants were sprayed with a 250-ppm solution of the test compound in acetone, water, and a small amount of a non-ionic emulsifier. The sprayed plants were then inoculated one day later with the organism, placed in an environmental chamber and incubated at 66°–68° F and 100% relative humidity for at least 16 hours. Following the incubation, the plants were allowed to dry and then were maintained at 60–80% relative humidity for approximately 7 days. The percent disease control provided by a given test compound was based on the percent disease reduction relative to untreated check plants. The test compounds and the results are tabulated in Table III.

EXAMPLE 8

Tomato Early Blight

Representative compounds of the invention were tested for the control of the Tomato Early Blight organism, *Alternaria solani conidia*. Tomato (variety Bonny Best) seedlings of 6 to 7 weeks old were used. The tomato plants were sprayed with a 250-ppm solution of the test compound in an acetone-and-water solution containing a small amount of a non-ionic emulsifier. The sprayed plants were inoculated one day later with the organism, dried and maintained at 60–80% relative humidity for about 12 days. Percent disease control was based on the percent disease development on untreated check plants. The compounds tested and the results are tabulated in Table IV.

EXAMPLE 9

Celery Late Blight

Representative compounds of the invention were tested for the control of Celery Late Blight using celery (Utah) plants 11 weeks old. The Celery Late Blight organism was *Septoria apii*. The celery plants were sprayed with solutions of the candidate toxicant mixed with acetone, water and a nonionic emulsifier. The plants were then inoculated with the organism and placed in an environmental chamber and incubated at 66°–68° F in 100% relative humidity for an extended period of time (approximately 48 hours). Following the incubation, the plants were allowed to dry and then were maintained at a 60–80% relative humidity for approximately 14 days. The percent disease control provided by a given candidate toxicant is based on the percent disease reduction relative to untreated check plants. The results are reported in Table V.

EXAMPLE 10

Powdery Mildew Control

Representative compounds of the invention were tested for powdery mildew control using pinto-bean plants. The pathogen was *Erysiphe polygoni*. The pinto-bean plants were sprayed with a 250-ppm solution of the test compound in an acetone-water mixture containing a nonionic emulsifier. One day after spraying, the treated plants were inoculated with the pathogen and then maintained in a greenhouse at a 60–80% relative humidity. The rate of infection on the leaves was determined after about 10 days. The percent disease control provided by a given test compound was based on the disease reduction relative to untreated check plants. The results are reported in Table VI.

TABLE I

Compounds of the formula

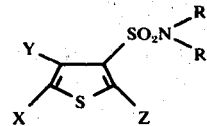

($\phi$ represents phenyl)

| No. | Y | X | Z | R¹ | R² | Melting Point °C. | % Sulfur Calc. | % Sulfur Found | % Chlorine Calc. | % Chlorine Found |
|---|---|---|---|---|---|---|---|---|---|---|
| 1 | H | Cl | Cl | $\phi$ | H | 109–110 | 20.8 | 20.7 | 23.0 | 22.8 |
| 2 | H | Cl | Cl | p-Cl-$\phi$ | H | 108–109 | 18.7 | 18.8 | 31.0 | 29.9 |
| 3 | H | Cl | Cl | i-C₃H₇ | H | 65–66 | 23.4 | 23.1 | 25.9 | 26.3 |
| 4 | H | Cl | Cl | p-CH₃-$\phi$ | H | 69–70 | 19.9 | 19.6 | 22.0 | 21.3 |
| 5 | H | Cl | Cl | 3,5-Cl₂-$\phi$ | H | 135–136 | 17.0 | 16.1 | 37.6 | 36.9 |
| 6 | Cl | Cl | Cl | CH₃ | H | 112–114 | 22.9 | 22.4 | 37.9 | 42.3 |
| 7 | Cl | Cl | Cl | $\phi$ | H | 138–139 | 18.7 | 17.6 | 31.0 | 29.1 |
| 8 | Cl | Cl | Cl | p-CH₃-$\phi$ | H | 124–125 | 18.0 | 15.9 | 29.8 | 26.6 |
| 9 | H | Cl | Cl | CH₃ | H | 61–63 | 26.1 | 25.9 | 28.8 | 29.0 |
| 10 | NO₂ | Cl | Cl | CH₃ | H | 149–150 | 22.0 | 22.0 | 24.4 | 24.1 |
| 11 | NO₂ | Cl | Cl | $\phi$ | H | 127–129 | 18.2 | 18.3 | 20.1 | 20.4 |
| 12 | H | Cl | Cl | t-C₄H₉ | H | 113–114 | 22.3 | 22.2 | 24.6 | 25.3 |
| 13 | H | Cl | Cl | p-F-$\phi$ | H | 72–74 | 19.7 | 19.2 | 21.8 | 21.1 |
| 14 | H | Cl | Cl | p-I-$\phi$ | H | 94–69 | 14.8 | 14.3 | 16.3 | 16.1 |
| 15 | H | Cl | Cl | p-CF₃-$\phi$ | H | 102–103 | 17.0 | 17.0 | 18.9 | 20.3 |
| 16 | H | Cl | Cl | m-CF₃-$\phi$ | H | 98–99 | 17.0 | 17.6 | 18.9 | 19.2 |
| 17 | NO₂ | Cl | Cl | p-CF₃-$\phi$ | H | 160–163 | 15.2 | 14.7 | 16.8 | 15.3 |

TABLE I-continued

Compounds of the formula $$Y-\text{(thiophene)}-SO_2N(R^1)(R^2)$$ with X, Z on thiophene (φ represents phenyl)

| No. | Y | X | Z | R¹ | R² | Melting Point °C. | % Sulfur Calc. | % Sulfur Found | % Chlorine Calc. | % Chlorine Found |
|---|---|---|---|---|---|---|---|---|---|---|
| 18 | H | Cl | Cl | 3,5-(CF₃)₂-φ | H | 107–108 | 14.4 | 13.9 | 16.0 | 16.3 |
| 19 | H | Cl | Cl | CH₃ | —SCCl₂CCl₂H | 85–86 | 21.7 | 19.4 | 47.9 | 45.5 |
| 20 | H | Cl | Cl | CH₃ | —SCCl₃ | 89–91 | 24.3 | 24.5 | 44.8 | 43.4 |
| 21 | Cl | Cl | Cl | p-CH₃-φ | —SCCl₃ | 111–112 | 19.0 | 19.0 | 42.0 | 40.9 |
| 22 | H | Cl | Cl | φ | —SCCl₂CCl₂H | 170–173 | 19.0 | 18.9 | 42.0 | 41.1 |
| 23 | H | Cl | Cl | φ | —SCCl₃ | 110–112 | 21.0 | 20.7 | 38.7 | 38.6 |
| 24 | H | Cl | Cl | p-Cl-φ | —SCCl₃ | 94–95 | 19.6 | 18.6 | 43.2 | 40.6 |
| 25 | H | Cl | Cl | i-C₃H₇ | —SCCl₃ | 56–57 | 22.7 | 21.6 | 41.8 | 39.7 |
| 26 | H | Cl | Cl | C₂H₅ | —SCCl₃ | 54–55 | 23.5 | 23.3 | 43.3 | 41.8 |
| 27 | H | Cl | Cl | p-CH₃-φ | —SCCl₃ | 86–87 | 20.4 | 20.1 | 37.6 | 37.1 |
| 28 | H | Cl | Cl | 3,5-Cl₂-φ | —SCCl₃ | 111–113 | 18.3 | 17.7 | 47.1 | 51.4 |
| 29 | H | Cl | Cl | 2,6-(CH₃)₂-φ | —SCCl₃ | 121–122 | 19.0 | 19.0 | 36.5 | 35.0 |
| 30 | Cl | Cl | Cl | p-CH₃-φ | —SCCl₂CCl₂H | 132–133 | 17.3 | 17.6 | 44.8 | 43.6 |
| 31 | H | Cl | Cl | p-CF₃-φ | —SCCl₃ | 77–79 | 18.3 | 18.1 | 33.7 | 33.6 |
| 32 | H | Cl | Cl | p-CF₃-φ | —SCCl₂CCl₂H | 125–127 | 16.8 | 16.8 | 37.1 | 38.3 |
| 33 | H | Cl | Cl | 3,5-(CF₃)₂-φ | —SCCl₂CCl₂H | 108–110 | 15.0 | 15.1 | 33.1 | 34.1 |
| 34 | H | Cl | Cl | 3,5-(CF₃)₂-φ | —SCCl₃ | oil | 16.2 | 16.5 | 30.9 | 28.2 |
| 35 | H | Cl | Cl | p-F-φ | —SCCl₃ | 102–104 | 20.2 | 19.6 | 37.3 | 36.0 |
| 36 | NO₂ | Cl | Cl | CH₃ | —SCCl₃ | 126–128 | 21.8 | 21.4 | 40.2 | 38.4 |
| 37 | NO₂ | Cl | Cl | CH₃ | —SCCl₂CCl₂H | oil | 19.7 | 19.5 | 43.5 | 42.4 |
| 38 | NO₂ | Cl | Cl | φ | —SCCl₃ | 176–178 | 19.1 | 18.9 | 35.3 | 35.3 |
| 39 | NO₂ | Cl | Cl | φ | —SCCl₂CCl₂H | 118–120 | 17.5 | 17.6 | 38.6 | 36.6 |
| 40 | H | Cl | Cl | m-CF₃-φ | —SCCl₃ | oil | 18.3 | 18.0 | 33.7 | 32.6 |
| 41 | H | Cl | Cl | m-CF₃-φ | —SCCl₂CCl₂H | 80–82 | 16.7 | 15.8 | 37.0 | 36.0 |

TABLE II

Botrytis cinerea Control

| Compound No. | % Control |
|---|---|
| 2 | 56 |
| 3 | 27 |
| 7 | 33 |
| 8 | 33 |
| 15 | 100 |
| 18 | 30 |
| 20 | 56 |
| 21 | 73 |
| 23 | 79 |
| 24 | 44 |
| 26 | 27 |
| 30 | 33 |
| 31 | 36 |
| 32 | 53 |
| 33 | 45 |
| 34 | 45 |

TABLE III

Tomato Late Blight Control

| Compound No. | % Control |
|---|---|
| 1 | 35 |
| 2 | 50 |
| 3 | 37 |
| 8 | 77 |
| 10 | 79 |
| 12 | 73 |
| 14 | 50 |
| 15 | 75 |
| 19 | 44 |
| 20 | 63 |
| 21 | 34 |
| 25 | 71 |
| 26 | 71 |
| 30 | 34 |
| 31 | 97 |
| 32 | 95 |
| 37 | 79 |
| 39 | 91 |

TABLE IV

Tomato Early Blight Control

| Compound No. | % Control |
|---|---|
| 6 | 71 |
| 9 | 73 |
| 10 | 27 |
| 11 | 27 |
| 15 | 34 |
| 23 | 93 |
| 24 | 71 |
| 27 | 81 |
| 29 | 96 |
| 30 | 27 |
| 31 | 77 |
| 36 | 68 |
| 37 | 89 |
| 38 | 27 |

TABLE V

Celery Late Blight Control

| Compound No. | % Control |
|---|---|
| 3 | 44 |
| 4 | 40 |
| 15 | 71 |
| 17 | 33 |
| 18 | 97 |
| 19 | 44 |
| 24 | 39 |
| 33 | 100 |

TABLE V-continued

Celery Late Blight Control

| Compound No. | % Control |
|---|---|
| 34 | 91 |

TABLE VI

Powdery Mildew Control

| Compound No. | % Control |
|---|---|
| 2 | 33 |
| 3 | 27 |
| 4 | 74 |
| 7 | 100 |
| 8 | 100 |
| 13 | 44 |
| 15 | 63 |
| 16 | 64 |
| 17 | 56 |
| 18 | 100 |
| 19 | 90 |
| 21 | 99 |
| 23 | 100 |
| 24 | 92 |
| 27 | 100 |
| 28 | 99 |
| 29 | 100 |
| 30 | 69 |
| 31 | 85 |
| 32 | 44 |
| 33 | 100 |
| 34 | 100 |
| 35 | 99 |

What is claimed is:

1. A fungicidal composition comprising a fungicidally effective amount of a compound of the formula

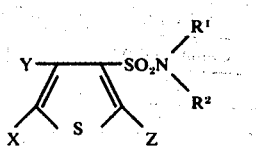

wherein X is nitro, fluoro, chloro or bromo; Y is hydrogen, nitro, fluoro, chloro or bromo; Z is nitro, fluoro, chloro or bromo; $R^1$ is alkyl of 1 to 6 carbon atoms, phenyl or phenyl substituted with up to 2 of the same or different substituents selected from the group consisting of trifluoromethyl, trichloromethyl, fluoro, chloro, bromo, iodo, nitro and alkyl of 1 to 3 carbon atoms; and $R^2$ is haloalkylthio of 1 to 2 carbon atoms and 2 to 5 of the same or different halogens selected from the group consisting of fluoro, chloro and bromo; and a biologically inert carrier.

2. The composition of claim 1 wherein X, Y and Z are the same halogen and are chloro or bromo.

3. The composition of claim 1 wherein Y is hydrogen or nitro and X and Z are the same halogen and are chloro or bromo.

4. The composition of claim 1 wherein $R^2$ is trichloromethylthio or tetrachloroethylthio.

5. The composition of claim 4 wherein the compound is 2,5-dichloro-3-(N-methyl-N-trichloromethylthiosulfonamido)-thiophene.

6. The composition of claim 1 wherein $R^1$ is phenyl substituted with 1 to 2 trifluoromethyl or trichloromethyl radicals.

7. The composition of claim 6 wherein Y is hydrogen or nitro and X and Z are the same halogen and are chloro or bromo.

8. The composition of claim 7 wherein Y is hydrogen, X and Z are chloro and $R^1$ is 4-trifluoromethylphenyl.

9. A method for controlling fungi which comprises contacting said fungi or their habitats with a fungicidally effective amount of the compound defined in claim 1.

10. The method of claim 9 where $R^2$ is trichloromethylthio or tetrachloroethylthio, and $R^1$ is phenyl substituted with 1 to 2 trifluoromethyl or trichloromethyl radicals.

11. A compound of the formula defined in claim 1.

12. The compound of claim 11 wherein $R^1$ is phenyl substituted with 1 to 2 trifluoromethyl or trichloromethyl radicals.

13. The compound of claim 12 wherein Y is hydrogen or nitro and X and Z are the same halogen and are chloro or bromo.

14. The compound of claim 13 wherein Y is hydrogen, X and Z are chloro and $R^1$ is 4-trifluoromethylphenyl.

15. The compound of claim 11 wherein Y is hydrogen, X and Z are chloro, $R^1$ is methyl and $R^2$ is trichloromethylthio.

* * * * *